(12) United States Patent
Abe et al.

(10) Patent No.: US 6,923,757 B2
(45) Date of Patent: Aug. 2, 2005

(54) ENDOSCOPE HAVING A LUBRICANT

(75) Inventors: Masanao Abe, Saitama (JP); Kazuhiko Gonda, Saitama (JP)

(73) Assignee: PENTAX Corporation, Tokyo (JP)

( * ) Notice: Subject to any disclaimer, the term of this patent is extended or adjusted under 35 U.S.C. 154(b) by 116 days.

(21) Appl. No.: 10/152,019

(22) Filed: May 22, 2002

(65) Prior Publication Data

US 2003/0023143 A1 Jan. 30, 2003

(30) Foreign Application Priority Data

May 22, 2001 (JP) ........................................ 2001-152545

(51) Int. Cl.$^7$ ............................. A61B 1/00; A61B 1/07
(52) U.S. Cl. ..................... 600/130; 600/182; 600/101
(58) Field of Search ................................. 600/101, 130, 600/139, 128, 153, 182; 385/115, 117

(56) References Cited

U.S. PATENT DOCUMENTS

| | | | | |
|---|---|---|---|---|
| 4,035,210 A | * | 7/1977 | Ohyoshi et al. | 216/24 |
| 4,707,392 A | * | 11/1987 | Kato et al. | 428/65.4 |
| 5,073,048 A | * | 12/1991 | Adachi et al. | 385/115 |
| 5,221,582 A | * | 6/1993 | Yamakawa | 428/425.9 |
| 5,483,951 A | * | 1/1996 | Frassica et al. | 600/104 |
| 5,716,322 A | | 2/1998 | Hui et al. | |
| 5,860,914 A | * | 1/1999 | Chiba et al. | 600/151 |
| 2001/0047124 A1 | * | 11/2001 | Yamamoto | 600/101 |

FOREIGN PATENT DOCUMENTS

| | | |
|---|---|---|
| JP | 58-77305 | 5/1983 |
| JP | 58-86132 | 5/1983 |
| JP | 6-40175 | 5/1994 |
| JP | 11-28184 | 2/1999 |
| JP | 11-309110 | 11/1999 |
| JP | 2001-302286 | 10/2001 |

OTHER PUBLICATIONS

English Language Abstract of JP 2001–302286.
English Language Abstract of JP 11–28184.
English Language Abstract of JP 11–309110.

* cited by examiner

*Primary Examiner*—John P. Leubecker
(74) *Attorney, Agent, or Firm*—Greenblum & Bernstein, P.L.C.

(57) ABSTRACT

An endoscope which has small bending resistance and is hard to be damaged or broken even when it is repeatedly used is disclosed. The endoscope includes a flexible insertion section 2 and an operation section 7 provided on the proximal end of the insertion section 2. The insertion section 2 has a sheath constructed from an outer layer 382 and the like, and elongated members such as an image guide 31 and light guides 32, 32 and the like are housed in lumens in the sheath. Further, each light guide 32 has an optical fiber bundle and a protective sheath 321 for protecting the optical fiber bundle. In the interior space of the protective sheath 321, a lubricant 5 containing a silicone oil and a solid lubricant is provided. The solid lubricant contains at least one of boron nitride, poly tetrafluoroethylene, and molybdenum disulfide. The solid lubricant is preferably formed into powder having an average grain size of 0.1 to 15 μm. By providing the lubricant 5 in the interior space of the lumen, bending resistance of the insertion section is reduced so that damage, breakage, or the like is hard to occur in the elongated members.

10 Claims, 4 Drawing Sheets

ENDOSCOPE HAVING A LUBRICANT

BACKGROUND OF THE INVENTION

1. Field of the Invention

This Invention relates to an endoscope.

2. Description of the Prior Art

In a medical field, an endoscope is used for examination or diagnosis of an alimentary canal and the like. This endoscope includes an insertion section which is to be inserted into a body cavity and an operation section which is provided on the proximal end of the insertion section for operating the distal portion of the insertion section to bend it. Further, this endoscope also includes a connection section. The connection section extends from the operation section, and the free end thereof is to be connected to a light source device or a control device.

Since the endoscope is inserted into a body cavity having curved portions, the insertion section thereof includes a flexible tube which is flexible so as to be bendable along the curves of the body cavity and a bendable part provided on the tip part of the flexible tube so as to be bendable with operation of the operation section.

Inside the insertion section of such an endoscope, elongated members are arranged so as to pass through the interior space of the insertion section along the longitudinal direction as needed. Examples of the elongated members include a bending mechanism for bending the bendable part which is provided on the tip part of the insertion section; a light guide for transmitting illumination light emitted from a light source device to the distal end of the insertion section; an image guide for transmitting an observation image to the operation section, a forceps tube for inserting a forceps, used for performing a treatment, cytotechnology, or the like, into a body cavity; an air and/or liquid supply tube for supplying chemicals and the like into the body cavity; and the like.

In the endoscope having the above structure, when the flexible tube or the bendable part is bent, friction is produced among the respective elongated members provided in the interior space of the insertion section due to the bending operation, and as a result, pressure is exerted on the respective elongated members. In order to protect the respective elongated members from the friction and the pressure, a lubricant is usually provided around the respective elongated members.

However, since conventional lubricants do not have sufficient lubricity, there is a case that the elongated members, in particular, optical fibers constituting the light guide and the image guide are damaged or broken due to repeated bending operations.

Further, there are known some conventional lubricants having relatively high lubricity. However, even when such a lubricant is used, a relatively large amount of lubricant is required in order to obtain sufficient lubricity. When such a large amount of lubricant is used, there is a case that the lubricant is easily changed in quality and deteriorated due to sterilization of the endoscope, whereby resulting in the case that lubricity thereof is lowered or the endoscope is broken.

SUMMARY OF THE INVENTION

It is therefore an object of the present invention to provide an endoscope which has small bending resistance and is hard to be damaged or broken due to repeated use.

In order to achieve the object mentioned above, the present invention is directed to an endoscope which comprises a plurality of lumens, each lumen having an interior space; at least one elongated member passing through the interior space of the lumen, and a lubricant provided in the interior space of the lumen. The lubricant includes a silicone oil and a solid lubricant containing at least one selected from the group consisting of boron nitride, polytetrafluoroethylene, and molybdenum disulfide.

According to the present invention described above, it is possible to provide an endoscope which has small bending resistance and is hard to be damaged or broken due to repeated use.

In the present invention, it is preferred that the elongated member can be moved relatively to the lumen. This makes the bending resistance of the endoscope still smaller.

Further, it is also preferred that the silicone oil is provided along substantially the entire length of the lumen or the elongated member. This makes the bending resistance of the endoscope still smaller, and enables to facilitate a process for inserting the elongated member into the lumen in manufacturing the endoscope.

Furthermore, it is also preferred that the solid lubricant is provided in at least a bendable part of an insertion section of the endoscope. According to this, it is possible to make the bending resistance of the endoscope still smaller, and to provide an endoscope which is particularly hard to be damaged or broken.

Moreover, it is also preferred that the lubricant is provided around the elongated member. This makes the bending resistance of the endoscope still smaller.

In the present invention, in a case where the elongated member is an optical fiber bundle, it is preferred that the silicone oil and the solid lubricant are provided on at least a part of the outer surface of the optical fiber bundle. This makes it possible to effectively prevent the optical fiber bundle from being damaged or broken.

In this case, it is also preferred that the silicone oil and the solid lubricant are provided on at least a part of the outer surface of respective optical fibers constituting the optical fiber bundle. This makes it possible to effectively prevent the optical fiber bundle from being damaged or broken.

In the present invention, it is preferred that the solid lubricant is formed into powder. According to this, it becomes easy to handle the lubricant, and the bending resistance of the endoscope also becomes still smaller.

In this case, it is also preferred that the average grain size of the solid lubricant is in the range of 0.1 to 15 $\mu$m. This also makes the bending resistance of the endoscope still smaller.

In the present invention, it is preferred that the solid lubricant is dispersed in the silicone oil. This also makes the bending resistance of the endoscope still smaller and improves durability of the endoscope. In addition, it becomes easy to handle the lubricant in manufacturing the endoscope.

Further, it is also preferred that the kinematic viscosity of the silicone oil at 25° C. is 10 to 500 cst. This also makes the bending resistance of the endoscope still smaller.

Furthermore, it is also preferred that the silicone oil contains modified silicone oils as a main ingredient. This also makes the bending resistance of the endoscope still smaller.

These and other objects, structures and advantages of the present invention will be apparent when the following description of the preferred embodiments will be considered taken in conjunction with the accompanying drawings.

DETAILED DESCRIPTION OF THE INVENTION

Hereinbelow, a preferred embodiment of an endoscope according to the present invention will be described in detail with reference to the accompanying drawings.

Figure 1:
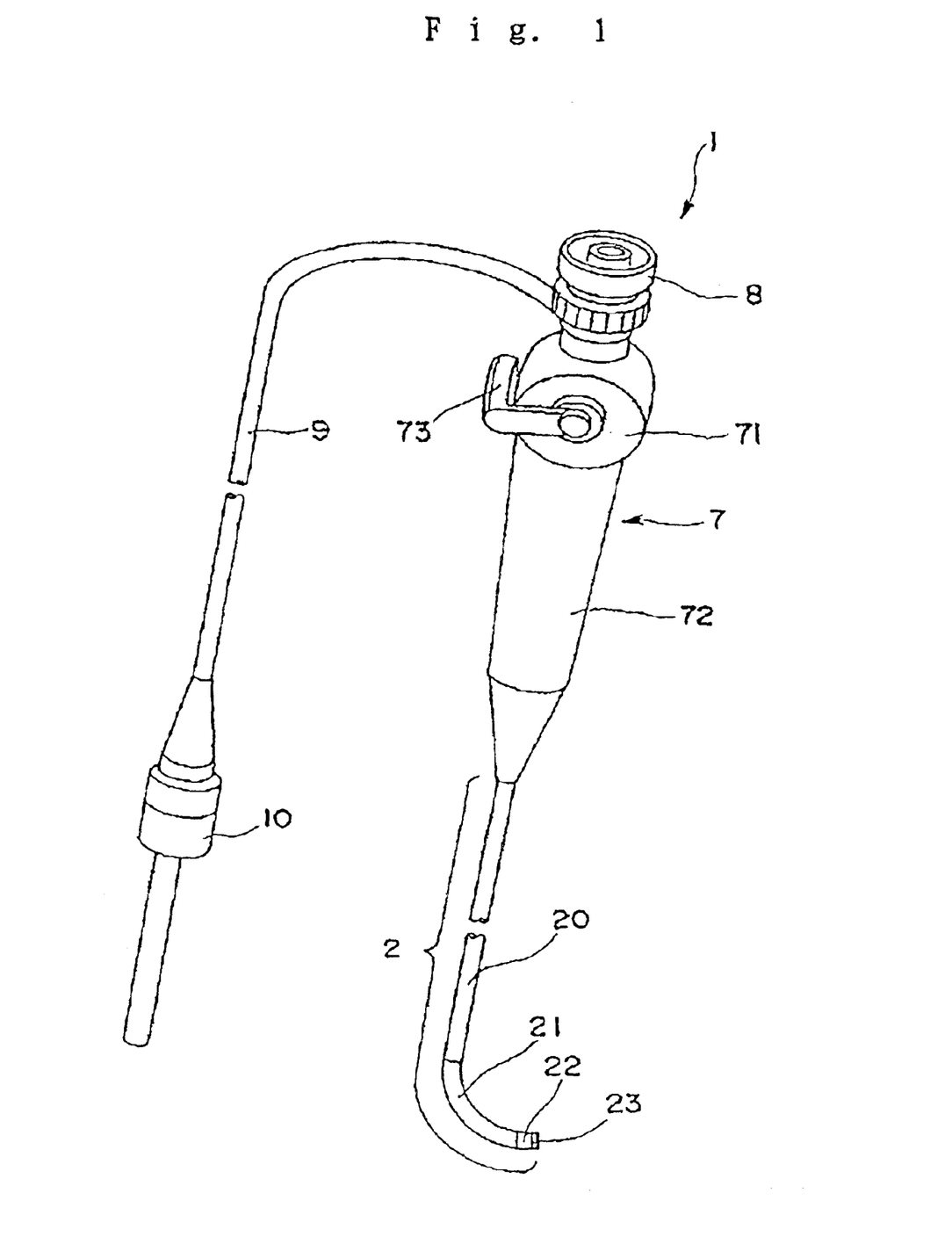
FIG. 1 is a perspective view which shows the overall structure of an embodiment of an endoscope according to the present invention.
Figure 2:
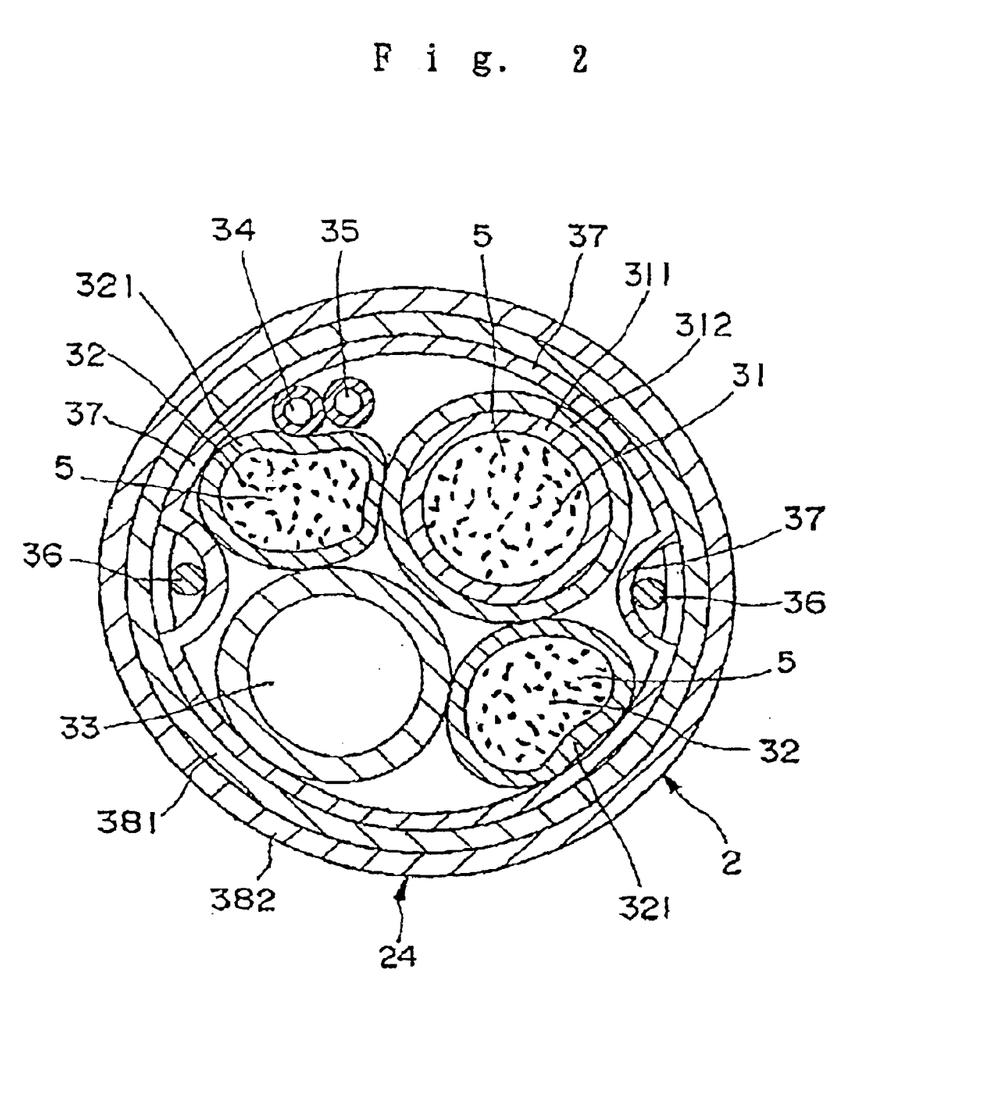
FIG. 2 is a cross sectional view of an insertion section of the endoscope shown in FIG. 1.
Figure 3:
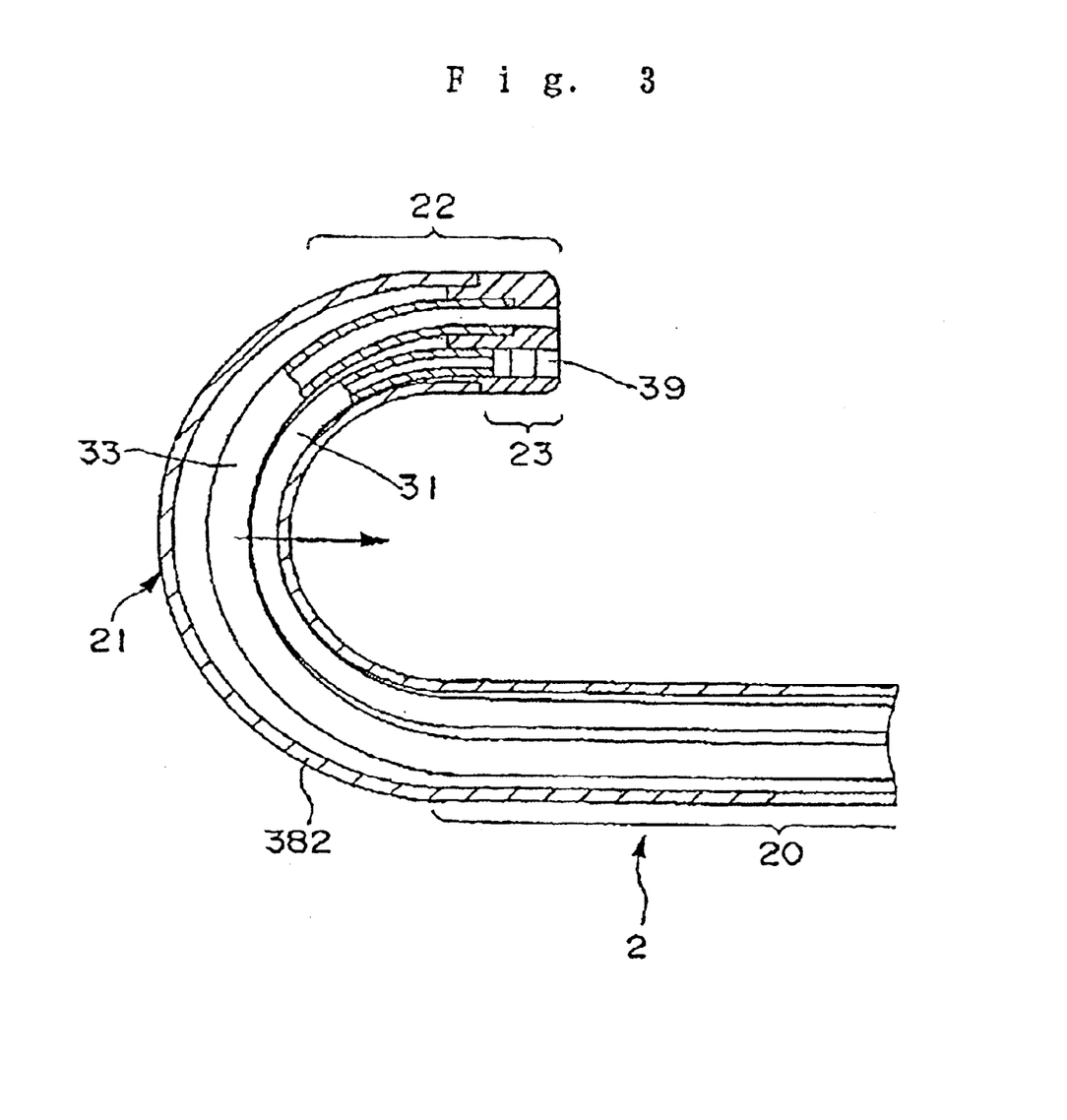
FIG. 3 is a longitudinal sectional view of a bendable part of the insertion section of the endoscope shown in FIG. 1.
Figure 4:
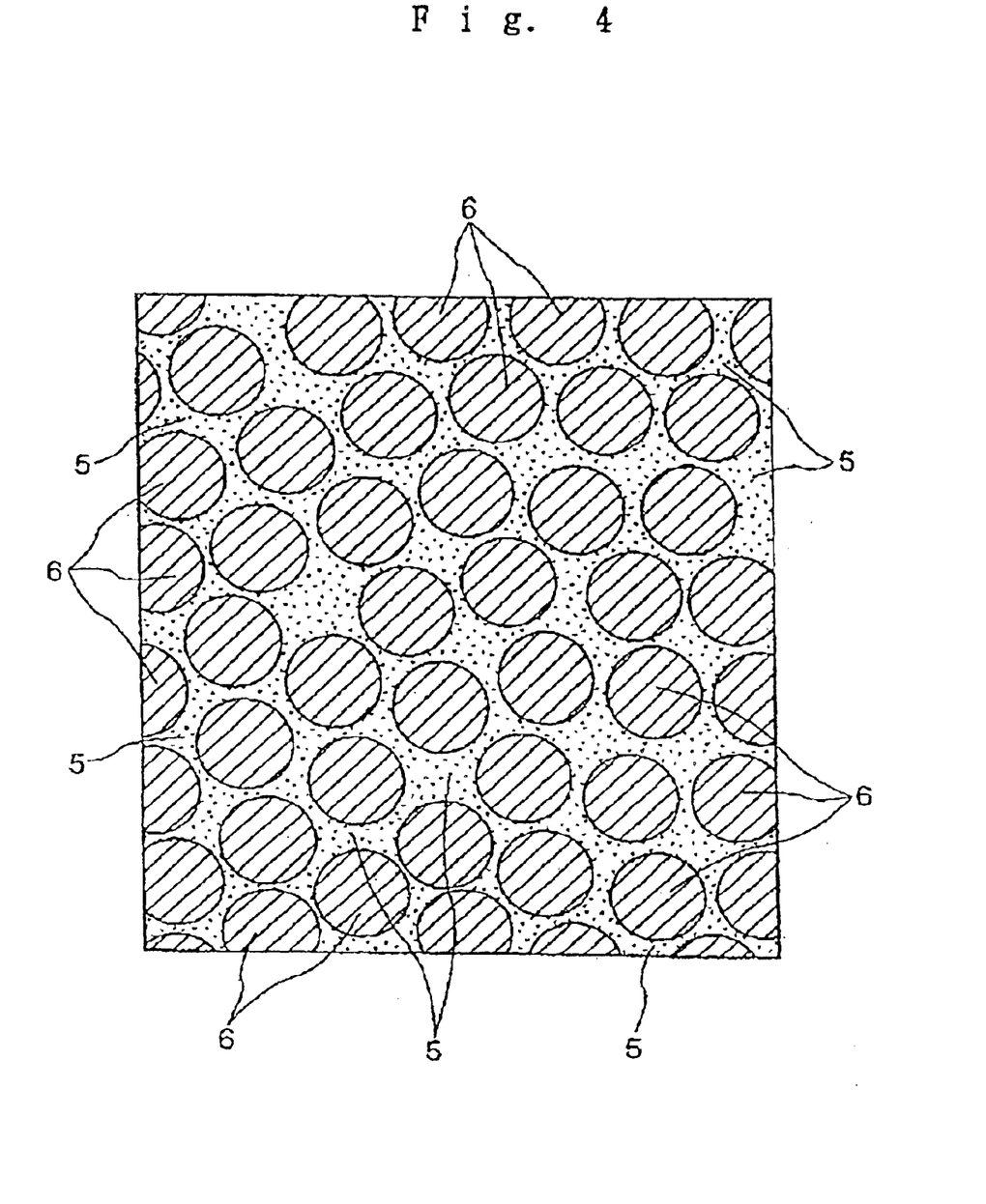
FIG. 4 is an enlarged sectional view which shows a part of the cross sectional view shown in FIG. 2.

FIG. 1 is a perspective view which shows the overall structure of an embodiment of an endoscope (fiber scope type) according to the present invention, FIG. 2 is a cross sectional view of a flexible tube of the endoscope shown in FIG. 1; FIG. 3 is a longitudinal sectional view of a bendable part of the endoscope shown in FIG. 1; and FIG. 4 is an enlarged cross sectional view of a part (in the vicinity of the central portion of an optical fiber bundle constituting a light guide) of the cross sectional view shown in FIG. 2. Hereinbelow, the upper side and the lower side in FIG. 1 will be referred to as "proximal end" and "distal end", respectively.

[Structure of Endoscope]

As shown in FIG. 1, the endoscope 1 of the present invention includes an elongated flexible (elastic) insertion section 2 and an operation section 7 which is provided on the proximal end of the insertion section 2. The operation section 7 is gripped by an operator during endoscope examination to manipulate the endoscope 1.

As shown in FIG. 1, the operation section 7 includes an operation section body 71 and a cover 72 which constitute the exterior of the operation section 7, a bending operation mechanism for remotely controlling bending operation of a bendable part 2, and an air and/or liquid supply channel from which fluids are introduced to the distal end of the insertion section 2.

Further, a bending operation lever 73 used for performing the bending operation of the bendable part 21 as described above is pivotally mounted to the operation section body 71. Also, a connection flexible tube 9 is connected at one end thereof to the operation section body 71 on the side which is opposite from the side where the bending operation lever 73 is mounted. In the interior space of the connection flexible tube 9, light guides 32, 32 (which will be described later) pass through. On the other hand, the free end (the other end) of the connection flexible tube 9 is connected to a connector 10, and this connector 10 is to be connected to a light source device (not shown).

Furthermore, an eyepiece 8 is provided on the top portion (proximal end) of the operation section body 71. By providing the eyepiece 8. It is possible to directly observe an observation image. Further, since this eyepiece 8 can be detachably connected to a CCD (imaging element) or a camera including optical image pickup (not shown), it is also possible to observe the observation image by displaying it on a screen of a monitor.

As shown in FIG. 1, the insertion section 2 includes a flexible tube 20 and the bendable part 21. The flexible tube 20 is provided on the distal end of the operation section 7, and the bendable part 21 is provided on the distal end of the flexible tube 20. Further, the bendable part 21 has a distal portion 22 and a distal end portion 23 provided in the tip part of the distal portion 22. When the endoscope 1 is used, such an insertion section 2 is inserted into a body cavity.

As shown in FIG. 2, an outer sheath 24 which defines the outer periphery of the insertion section 2 is constructed from a wire guide tube 37, an inner layer tube 381, and an outer layer 382, and they are laminated in this order from the inner side of the outer sheath 24 so that an interior space (lumens) is defined therein.

In the interior space of the outer sheath 24 of the insertion section 2, there are arranged a plurality of elongated members such as an image guide 31, the light guides 32, 32, a forceps tube 33. An air supply tube 34, and a liquid supply tube 35. These elongated members pass through the interior space (lumens) of the outer sheath 24 along the longitudinal direction thereof such that they are isolated from a body cavity by the outer sheath 24. Further, the outer sheath 24 prevents chemicals, body fluids, and the like which are in contact with the outer surface of the insertion section 2 from entering the interior space of the insertion section 2 to protect the respective elongated members housed therein.

The outer layer 382 of the outer sheath 24 is preferably constituted from a material having flexibility to prevent tissue in the body cavity from being damaged due to friction. Examples of the constituent material of the outer layer 382 include various resins having flexibility such as polyolefin based resins (e.g., polyvinyl chloride, polyethylene, polypropylene, ethylene-vinylacetate copolymers), polyamide based resins, polyester based resins (e.g., polyethylene terephthalate (PET) and polybutylene terephthalate), polyurethane based resins, polystyrene based resins, fluorine based resins (e g., polytetrafluoroethylene and ethylene-tetrafluoroethylene copolymers), polyimide based resins, and the like; and various elastomers such as polyurethane based elastomers, polyester based elastomers, polyolefin based elastomers, polyamide based elastomers, polystyrene based elastomers, fluorine based elastomers, silicone rubbers, latex rubbers, and the like. These materials can be used alone or in combination of two or more of them.

The thickness of the outer layer 382 is not limited to a specific value as long as the outer layer 382 can protect the respective members housed in the interior space of the insertion section 2 and dose not impair the flexibility and bending property of the insertion section 2, but it is preferably in the range of about 100 to 3,000 $\mu$m, and more preferably in the range of about 200 to 1,000 $\mu$m.

Hereinbelow, description will be made with regard to the respective elongated members (image guide 31, light guides 32, 32, forceps tube 33, air supply tube 34, liquid supply tube 35) housed in the interior space of the outer sheath 24.

As shown in FIG. 2, the image guide 31 is constructed from an optical fiber bundle and protective sheaths (a first protective sheath 311 and a second protective sheath 312) for protecting the optical fiber bundle. An observation image is sent to the eyepiece 8 through the image guide 31.

The optical fiber bundle is constituted from a plurality of optical fibers 6. Both ends of the optical fibers 6 are respectively tied by an adhesive or the like in a bundle to fix to the eyepiece 8 and to the distal end portion 23, respectively. On the other hand, portions other than the both ends of the optical fibers are in a state that they can be freely moved. Therefore, the cross sectional shape of the portion other than the both ends of the image guide 31 can be deformed as desired.

As shown in FIG. 3, an objective lens 39 is provided in the distal end portion 23 of the insertion section 2. The tip end of the image guide 31 (that is an end of the image guide 31 from which light is received) is connected to the objective lens 39.

An observation image is formed on the tip end of the image guide 31 by the objective lens 39.

As shown in FIG. 2, each of the light guides 32 is constructed from an optical fiber bundle and a protective sheath 321 for protecting the optical fiber bundle.

The optical fiber bundle is constituted from a plurality of the optical fibers 6. Both ends of the optical fibers 6 are respectively tied by an adhesive or the like in a bundle to fix to the connector 10 and to the distal end portion 23, respectively. On the other hand, portions other than the both ends of the optical fibers 6 are in a state where they can be freely moved. Therefore, the cross sectional shape of the portions other than the both ends of the light guide 32 can be deformed as desired.

Light emitted from a light source device (not shown), which is connected with the connector 10, passes through each light guide 32, and then the light is irradiated toward the front of the distal end portion 23. This makes it possible to obtain illumination light for observing a subject.

The optical fiber 6 constituting the image guide 31 and the light guides 32, 32 is made of quartz, multi-component glass, plastic, or the like.

The diameter of the optical fiber 6 constituting the optical fiber bundle is not limited to a specific value, but it is preferably in the range of about 2 to 40 $\mu$m, and more preferably in the range of about 4 to 10 $\mu$m. If the diameter of the optical fiber 6 is less than the above lower limit value, there is a case that it is difficult to charge a lubricant 5 among the respective optical fibers of the optical fiber bundle. On the other hand, if the diameter of the optical fiber 6 exceeds the above upper limit value, there is a case that the density of the imaging elements and the light transmitting efficiency are lowered.

As described above, each elongated optical fiber bundle which constitutes the elongated member as claimed is housed within a lumen of the protective sheath 321. Further, as shown in FIG. 4, the lubricant 5 is provided so as to surround the respective optical fibers 6 of the optical fiber bundle. The lubricant 5 has excellent lubricity as will be described later in more detail.

By providing the lubricant 5 having excellent lubricity around the respective optical fibers 6 constituting the optical fiber bundle, friction resistances among the respective optical fibers 6 and between the protective sheath 321 and the optical fibers 6 are reduced at the time when the optical fibers 6 are relatively moved with respect to the protective sheath 321 (e.g., at the time when the insertion section 2 is bent). This enables the optical fibers 6 to be smoothly moved so that bending resistance of the insertion section 2 is reduced. Therefore, tension and stress exerted on the respective optical fibers 6 at the time when the insertion section 2 is bent are reduced and therefore buckling is suppressed, thereby enabling to effectively prevent damage, breakage, or the like of the light guide 32.

Similarly to the light guide 32, within the protective sheath of the image guide 31, the lubricant 5 is provided so as to surround the respective optical fibers 6 of the optical fiber bundle. This reduces friction resistances among the respective optical fibers 6 and between the first protective tube 311 and the optical fibers 6 at the time when the optical fibers 6 are relatively moved with respect to the first protective sheath 311 (e.g., at the time when the insertion section 2 is bent). Because of this, the respective optical fibers 6 can be smoothly moved so that bending resistance of the insertion section 2 is reduced. Therefore, as is the same with the case of the light guide 32, tension and stress exerted on the respective optical fibers at the time when the insertion section 2 is bent are reduced and therefore buckling is suppressed, thereby enabling to effectively prevent damage, breakage, or the like of the image guide 31.

The forceps tube 33 is formed into a hollow tubular shape, and a forceps is inserted into the hollow space. Various surgical procedures, treatments, or the like can be performed at an area of a body cavity in the vicinity of the distal end portion 23 of the endoscope 1 by using the inserted forceps.

In this regard, it is to be noted that medical treatment instruments, diagnosis instruments, or the like other than a forceps may also be inserted into the forceps tube 33.

The air supply tube 34 and the liquid supply tube 35 have openings at the distal end of the insertion section 2, respectively. Therefore, it is possible to supply fluids into a body cavity and to suck the fluids from the body cavity through the openings. For example, washing water, chemicals, or the like which has been introduced from the air and/or liquid supply channel provided in the operation section 7 is supplied, through the liquid supply tube 35, to an area of a body cavity in the vicinity of the distal end portion 23 of the endoscope 1 which has been inserted and then set in the body cavity. Also, body fluids or the like can be collected from an area of a body cavity in the vicinity of the distal end portion 23 of the endoscope 1 which has been inserted and then set in the body cavity.

The bendable part 21 in which such respective elongated members are housed can be bent in a predetermined direction (see FIG. 3) by turning the bending operation lever 73 to pull or loose a pair of wires 36 (described below).

Specifically, these wires 36 are arranged so that they are roughly diametrically opposite to each other through the central axis of the insertion section 2. Each wire 36 (elongated member) is inserted into a space (that is a lumen) formed between the wire guide 37 and the inner layer 381. The distal end of the wire 36 is bonded to a plugged portion in the distal portion 22 to fix it thereto.

Therefore, by turning the bending operation lever 73 to pull one of the wires 36 and to loose the other wire 36, the bendable part 21 is bent toward the side where the pulled wire 36 is positioned.

Further, the insertion section 2 can rotate about its axis with operation of the operation section 7. Therefore, combination of the rotating operation of the insertion section 2 and the bending operation of the bendable part 21 enables to observe a body cavity over 360 degrees.

The wire 36 is formed from a material having enough strength and durability not to cause breakage of the wire even if the wire is repeatedly pulled, and having a slight degree of elongation. Examples of the wire formed from such a material include a metal wire made of stainless steel; a fiber wire or a fiber bundle of resin fibers made of polyamide, polyester; and the like.

Further, the outer diameter of the wire 36 varies depending on the material of the wire 36 and on the conditions such as cross sectional shape, dimension, and constituent material of the insertion section 2. For example, in a case where the wire 36 is formed from stranded fibers made of polyacrylate or from a single wire of stainless steel, the outer diameter of the wire 36 is preferably in the range of about 30 to 3,000 $\mu$m, and more preferably in the range of about 100 to 1,000 $\mu$m.

As described above, the wire guide 37 holds the wire 36 together with the inner layer 381. Since the wire 36 is held by means of both the wire guide 37 and the inner layer 381, it can be smoothly bent to a predetermined direction.

Each of the wire guide 37 and the inner layer 381 is formed from a material (e.g., stainless steel) having enough strength and durability to reliably hold the wire 36 and not to be damaged when the wire 36 is pulled.

The thicknesses of the wire guide 37 and the inner layer 381 are not limited to specific values as long as the wire guide 37 and the inner layer 381 can hold the wire 36 and do not impair the flexibility and bending property of the insertion section 2, but they are preferably in the range of about 100 to 3,000 µm, and more preferably in the range of about 100 to 200 µm.

[Lubricant]

The feature of the present invention resides in the composition of the lubricant 5. Specifically, the lubricant of the present invention includes a silicon oil, and a solid lubricant containing at least one of boron nitride (BN), polytetrafluoroethylene, and molybdenum disulfide.

The lubricant 5 containing the silicone oil and the solid lubricant has especially excellent lubricity. Therefore, by using the lubricant 5, it becomes possible to significantly reduce bending resistance of the insertion section 2, thereby effectively preventing damage, breakage, or the like of the optical fibers 6 constituting the image guide 31 and the light guides 32, 32.

In the meantime, there is a case where the endoscope is subjected to high level sterilization by using a hydrogen peroxide based sterilizing agent or the like prior to or after its use. Some conventional lubricants used for the insertion section of the endoscope react with such a sterilizing agent, which results in deterioration and corrosion of the insertion section so that the endoscope can not be used for a long period of time.

On the other hand, the lubricant 5 of the present invention has especially excellent chemical resistance. For this reason, the lubricant 5 is hard to be changed in quality and deteriorated even when it comes in contact with such a sterilizing agent. Therefore, by using such a lubricant 5 for the endoscope 1, it becomes possible to use the endoscope 1 for a long period of time without deterioration even when the endoscope is used under a condition where it usually comes in contact with chemicals such as a sterilizing agent.

As described above, the lubricant 5 has the excellent lubricity as well as the excellent chemical resistance. Therefore, a synergistic effect of the lubricity and the chemical resistance makes it possible to provide an excellent endoscope 1 as will be described later.

Hereinbelow, a detailed description will be made with regard to the solid lubricant and the silicone oil to be contained in the lubricant 5.

1. Solid Lubricant

As described above, the lubricant 5 contains the solid lubricant containing at least one of boron nitride (BN), polytetrafluoroethylene, and molybdenum disulfide.

The reason why such a solid lubricant is used in the present invention is given below.

Specifically, boron nitride (BN), polytetrafluoroethylene, and molybdenum disulfide have especially excellent lubricity, and they are preferably matched with a silicon oil as will be described later. Therefore, when the solid lubricants are used in combination with a silicone oil, a mixture of them exhibits conspicuous synergistic effect. For this reason, the lubricant 5 of the present invention can have excellent lubricity as compared with the case where other solid lubricants are used, and thereby the endoscope 1 can also have improved durability.

Therefore, by using the lubricant 5 containing the solid lubricant described above, it becomes possible to effectively reduce bending resistance of the insertion section 2 so that damage, breakage, or the like is hard to occur in the optical fibers 6 constituting the image guide 31 and the light guides 32, 32, even when the endoscope 1 is repeatedly used.

In particular, when the lubricant 5 contains boron nitride as the solid lubricant, since boron nitride is hard to absorb water, the lubricant 5 can maintain the excellent lubricity even when the endoscope 1 is repeatedly subjected to steam sterilization, for example.

Likewise, when the lubricant 5 contains polytetrafluoroethylene as the solid lubricant, since polytetrafluoroethylene is hard to absorb water, the lubricant 5 can maintain the excellent lubricity even when the endoscope 1 is repeatedly subjected to steam sterilization, for example.

Furthermore, when the lubricant 5 contains molybdenum disulfide as the solid lubricant, the lubricant 5 can obtain especially excellent lubricity.

In this case, the content (compositional ratio) of molybdenum disulfide contained in the lubricant 5 is preferably equal to or less than 8 wt %. And more preferably equal to or less than 3 wt %. If the content of molybdenum disulfide exceeds 8 wt %, there is a case that the lubricant 5 can not obtain enough chemical resistance depending on sterilization methods, sterilization conditions, and the like.

The form of the solid lubricant is not limited to a specific one, but the solid lubricant is preferably formed into powder. This is because the solid lubricant in the form of powder can enter into in narrow spaces among the optical fibers so as to exhibit excellent lubricity. Further, such solid lubricant can be easily handled.

In this case, the average grain size of the powder is not limited to a specific value, but it is preferably in the range of 0.1 to 15 µm, and more preferably in the range of 0.1 to 8 µm, for example.

If the average grain size is less than the above lower limit value, it becomes difficult to manufacture the solid lubricant. Further, handling of the solid lubricant becomes difficult.

On the other hand, if the average grain size exceeds the above upper limit value, there is a case that the lubricant can not obtain sufficient lubricity.

In this regard, it is to be noted that the lubricant may contain other solid lubricants (e.g., graphite, fluorocarbon $((CF)_n)$, or the like) in addition to boron nitride, polytetrafluoroethylene, or molybdenum disulfide.

2. Silicone Oil

Silicone oil exhibits a synergistic effect as will be described below in more detail when it is used in combination with the solid lubricant.

The silicone oil has excellent wettability to the solid lubricant and excellent chemical stability. For this reason, in the lubricant 5, the silicone oil surrounds the solid lubricant, thereby effectively preventing the solid lubricant from being deteriorated with a lapse of time (e.g., chemical changes, fracture, and the like). Therefore, the solid lubricant can stably maintain lubricity for a long period of time. With this result, the lubricant 5 can have excellent lubricity for a long period of time so that the endoscope 1 can have excellent durability.

Further, the silicone oil also has excellent repellency. For this reason, even when the endoscope 1 is subjected to high level sterilization by using a hydrogen peroxide based sterilization agent and it permeates into the inside of the insertion section 2, it is possible to effectively prevent the hydrogen peroxide based sterilization agent from coming in contact with the solid lubricant. Therefore, even when a solid lubricant having relatively low chemical resistance is used for the lubricant, it is possible to protect the solid lubricant from the hydrogen peroxide based sterilization agent, thereby effectively preventing the solid lubricant from being changed in quality and deteriorated.

As described above, by using the lubricant 5 containing the silicone oil, it is possible to effectively prevent the solid lubricant having excellent lubricity from being deteriorated even when the endoscope 1 is repeatedly subjected to the high level sterilization. Further, as described above, the silicone oil has excellent wettability to the optical fibers 6, the protective sheath, and the like. For this reason, the lubricant 5 (i.e., silicone oil and solid lubricant) keeps on contacting with the outer surface of the optical fiber 6 and the inner wall of the protective sheath, even when the insertion section 2 is repeatedly bent. Therefore, it is possible to maintain the excellent lubricity for a long period of time.

Furthermore, the silicone oil also has excellent lubricity in itself. Therefore, even when the content of the solid lubricant to be contained in the lubricant 5 is relatively small, the lubricant 5 can obtain sufficient lubricity as a whole.

Moreover, the silicone oil has excellent wettability to the optical fiber 6, the protective sheath, and the like as described above. For this reason, use of the lubricant 5 containing the silicone oil facilitates a process for covering the optical fiber bundle with the protective sheath in manufacturing the endoscope 1 and the like.

As has been described above, in the present invention, the lubricant 5 exhibits a synergistic effect by using the solid lubricant in combination with the silicone oil. That is, the lubricant 5 has an effect that exceeds the sum of the respective effects of the solid lubricant and the silicone oil.

Examples of the silicone oil include straight silicone oils such as dimethyl silicone oil (polysiloxane), methylphenyl silicone oil, and methyl hydrogen polysiloxane; and modified silicone oils such as epoxy modified silicone oil, alkyl modified silicone oil, amino modified silicone oil, carboxyl modified silicone oil, alcohol modified silicone oil, fluorine modified silicone oil, alkyl-aralkyl-polyether modified silicone oil, epoxy-polyether modified silicone oil, and polyether modified silicone oil. These silicone oils can be used alone or in combination of two or more of them in the present invention.

In this case, it is preferred that the silicone oil contains modified silicone oils as a main ingredient, because modified silicone oils have especially excellent heat resistance and lubricity.

Further, the kinematic viscosity of the silicone oil at 25° C. is preferably in the range of 100 to 500 cst, and more preferably in the range of 100 to 350 cst. By setting the kinematic viscosity of the silicone oil to the above range, the lubricant can obtain especially excellent lubricity, thereby effectively preventing the damage, breakage, and the like of the optical fiber bundle and other parts.

Furthermore, the silicone oil may contain additives such as heat resistance improving agent, stain, metallic soap, and the like.

Although the solid lubricant and the silicone oil to be contained in the lubricant 5 have been described above, the lubricant 5 may contain components (materials) other than the solid lubricant and the silicone oil. For example, the lubricant 5 may contain various additives such as calcium carbonate, silica, and the like.

Further, in the lubricant 5, it is preferred that the solid lubricant is dispersed in the silicone oil. This makes the synergistic effect of the solid lubricant and the silicone oil more conspicuous. As a result, the lubricant 5 can have excellent lubricity for a long period of time so that the endoscope 1 can have excellent durability. In addition, by using such a lubricant 5, it becomes easy to handle the lubricant 5 in manufacturing the endoscope 1.

As described above, the lubricant 5 is provided within the lumens (e.g., the periphery of the respective optical fibers 6) of the protective sheaths (the protective sheath 321 and the first protective sheath 311).

The lubricant 5 may be provided within only a part of each lumen, but it is preferred that the lubricant 5 is provided within the lumen along substantially the entire length of the optical fiber bundle (elongated member) or the protective sheath (lumen). By doing so, the insertion section 2 can obtain more excellent lubricity. As a result, in the endoscope 1, bending resistance of the insertion section 2 is reduced so that damage, breakage, or the like of the optical fibers 6 is hard to occur.

Further, the composition (mixing ratio of the respective components or the like) of the lubricant 5 may be the same in all areas within the lumen or it may vary according to areas within the lumen.

For example, assuming that the protective sheath 321 (optical fiber bundle) has two different areas along the longitudinal direction thereof and they are referred to as a first area and a second area, respectively, the lubricant 5 to be provided in the first area can be constituted from both the solid lubricant and the silicone oil and the lubricant 5 to be provided in the second area can be constituted from the silicone oil only. Further, the protective sheath 321 may have a third area other than the two areas described above, and in such a case the lubricant 5 to be provided in the third area may be constituted from the solid lubricant only.

As apparent from the above description, in the present invention, it is required that the lubricant 5 containing both the solid lubricant and the silicone oil is provided within at least a part of the lumen.

As described above, the lubricant 5 is provided within at least a part of the lumen. For this reason, the silicone oil constituting the lubricant 5 may also be provided within only a part of the lumen, but the silicone oil is preferably provided within the lumen along substantially the entire length of the optical fiber bundle (elongated member) or the protective sheath (lumen). This reduces bending resistance of the insertion section 2 even further, and enables to facilitate a process for covering the optical fiber bundle with the protective sheath in manufacturing the endoscope 1.

Further, similar to the silicone oil, the solid lubricant may be provided within only a part of the lumen. In this regard, it is preferred that the solid lubricant is provided within at least the bendable part 21 of the insertion section 2. By providing the solid lubricant in the bendable part 21, the following effects can be obtained.

The bendable part 21 of the insertion section 2 is bent with operation of the operation section 7, and at this time the radius of curvature of the bendable part 21 is especially small as compared with the other parts of the insertion section 2. That is, the bendable part 21 requires the highest lubricity in the insertion section 2. For this reason, by providing the solid lubricant in the bendable part 21, it becomes possible to reduce bending resistance of the insertion section 2 so that damage, breakage, or the like of the optical fibers 6 is hard to occur in the endoscope 1. In particular, when both the solid lubricant and the silicone oil are provided in the bendable part 21, the synergy effect of the solid lubricant and the silicone oil described above can be obtained in the bendable part 21.

As described above, by using the lubricant 5, bending resistance of the insertion section 2 is reduced so that damage, breakage, or the like of the optical fibers is hard to occur even when the endoscope 1 is repeatedly used.

In addition, by using the lubricant 5, the insertion section 2 can obtain excellent chemical resistance. Therefore, the insertion section 2 is hard to be deteriorated even when it is subjected to chemicals such as sterilization agent or the like, thus enabling to repeatedly disinfect or sterilize the endoscope 1 by using the chemicals or the like.

These effects described above become more conspicuous by appropriately selecting the kind of the solid lubricant and the silicone oil and then setting their contents.

The endoscope according to the present invention has been described; however this invention is not limited thereto.

For example, the lubricant 5 may be provided within lumens other than the lumens of the protective sheath 321 and the first protective sheath 311. That is, since the lubricant 5 of the present invention is provided within any lumens in which elongated members are housed, the lubricant 5 may be provided within lumens other than the lumens of the protective sheaths.

As described above, in the interior space (lumens) of the outer sheath 24, the elongated members such as the image guide 31, light guides 32, 32, forceps tube 33, air supply tube 34, and liquid supply tube 35 are housed. Therefore, the lubricant 5 may be provided in the interior space of the outer sheath 24, that is within the lumens in the outer sheath 24 (e.g., the peripheries of the image guide 31, light guides 32, 32, forceps tube 33, air supply tube 34, and liquid supply tube 35, and the like).

In this way, by providing the lubricant 5 in the interior space of the outer sheath 24, friction resistances among the respective elongated members and between the outer sheath and the respective elongated members can be also reduced at the time when the respective elongated members (image guide 31, light guides 32, 32, forceps tube 33, air supply tube 34, liquid supply tube 35) are relatively moved with respect to the outer sheath 24 (lumen). Therefore, the respective elongated members can be smoothly moved so that bending resistance of the insertion section 2 is reduced. As a result, it becomes possible to effectively prevent damage, breakage, or the like of the respective elongated members.

Further, as described above, since each of the wires 36 (elongated members) is inserted into the space (lumen) formed between the wire guide 37 and the inner layer 381, the lubricant may also be provided in this space (lumen) (e.g., the periphery of each wire 36).

In this way, by providing the lubricant 5 in the space (lumen) formed between the wire guide 37 and the inner layer 381 (e.g., the periphery of the wire 36 or the like), friction resistance between the inner wall of the lumen and the wire at the time when each wire 36 (elongated member) is relatively moved with respect to the lumen (e.g., in a case where the wire 36 is pulled) is reduced. Therefore, bending resistance of the insertion section 2 is further reduced. As a result, it becomes possible to smoothly pull each wire 36, thereby improving the manipulation of the endoscope 1 at the bending operation and the followability of the endoscope 1.

Further, the lubricant 5 may be provided not only within the lumens but also to a part other than the lumens such as slidable parts in the operation section 7.

Furthermore, the number of the wire 36 is not limited to two as described above. For example, only one wire or three or more wires may be used.

Moreover, it is possible to make various changes and additions to respective components of the endoscope of the present invention as long as the same functions are achieved.

For example, although the above embodiment has been described with reference to the case where the present invention is applied to an optical endoscope in which an optical fiber bundle is used as an image guide, the present invention is not limited thereto. The present invention can be applied to an electronic endoscope which has a CCD (image element) in its distal portion.

Also, the present invention may be applied to endoscopes for industrial use other than the endoscopes for medical use described above.

EXAMPLES

Hereinbelow, examples of the present invention will be described.

1. Manufacture of Endoscope

Example 1

An endoscope as shown in FIGS. 1 to 4 was manufactured by using a bronchofiberscope ("FB-15X" manufactured by Asahi Kougaku Kougyou Kabusiki Kaisha).

A lubricant was provided in the interior space of the protective sheath (i.e., substantially the entire periphery of the optical fiber bundle and respective optical fibers constituting the optical fiber bundle) along substantially the entire length thereof.

Further, in the endoscope, the lubricant provided in the bendable part contained both a solid lubricant and a silicone oil, and the lubricant provided in portions other than the bendable part contained the silicone oil only.

Powdery boron nitride (having an average grain size of 2 $\mu$m) was used as the solid lubricant, and fluorine-modified silicone oil (having a kinematic viscosity of about 200 cst at 25° C.) was used as the silicone oil.

At this time, the content of boron nitride (BN) contained in the lubricant for the bendable part was 5 wt %.

Example 2

An endoscope was manufactured in the same manner as in Example 1 except that polytetrafluoroethylene (PTFE) was used as the solid lubricant.

At this time, the content of polytetrafluoroethylene contained in the lubricant for the bendable part was 5 wt %.

Example 3

An endoscope was manufactured in the same manner as in Example 1 except that molybdenum disulfide ($MoS_2$) was used as the solid lubricant.

At this time, the content of molybdenum disulfide contained in the lubricant for the bendable part was 2 wt %.

Example 4

An endoscope was manufactured in the same manner as in Example 1 except that a lubricant having substantially uniform composition was provided along substantially the entire length of the protective sheath. Specifically, the lubricant had the constant mixing ratio of the solid lubricant and the silicone oil along substantially the entire length of the protective sheath.

Further, the solid lubricant was dispersed in the silicone oil along substantially the entire length of the protective sheath.

At this time, the content of boron nitride (BN) contained in the lubricant was 5 wt %.

Example 5

An endoscope was manufactured in the same manner as in Example 4 except that polytetrafluoroethylene (PTFE) was used as the solid lubricant.

At this time, the content of polytetrafluoroethylene contained in the lubricant was 5 wt %.

Example 6

An endoscope was manufactured in the same manner as in Example 4 except that molybdenum disulfide ($MoS_2$) was used as the solid lubricant.

At this time, the content of molybdenum disulfide contained in the lubricant was 2 wt %.

Example 7

An endoscope was manufactured in the same manner as in Example 1 except that a mixture of 50 wt % of boron nitride (BN) and 50 wt % of polytetrafluoroethylene (PTFE) was used as the solid lubricant provided in the bendable part, and boron nitride (BN) was used as the solid lubricant provided in portions other than the bendable part.

At this time, the content of the solid lubricant contained in the lubricant was 5 wt %.

Comparative Example 1

An endoscope was manufactured in the same manner as in Example 4 except that only the silicone oil was used as the lubricant (i.e., the lubricant did not contain any solid lubricant).

Comparative Example 2

An endoscope was manufactured in the same manner as in Example 4 except that only boron nitride (BN) was used as the lubricant (i.e., the lubricant did not contain any silicone oil).

Comparative Example 3

An endoscope was manufactured in the same manner as in Example 5 except that only polytetrafluoroethylene (PTFE) was used as the lubricant (i.e., the lubricant did not contain any silicone oil).

Comparative Example 4

An endoscope was manufactured in the same manner as in Example 6 except that only molybdenum disulfide ($MoS_2$) was used as the lubricant (i.e., the lubricant did not contain any silicone oil), 2. Evaluation For each of the endoscopes manufactured in respective Examples and Comparative Examples, the following evaluations were made.

(2-1) Covering Property with Protective Sheath

Covering property at the time when the optical fiber bundle is covered with the protective sheath (that is, easiness at the time when the optical fiber bundle is covered with the protective sheath) in manufacturing the endoscope was evaluated according to the four criteria given below.

A: Extremely excellent
B: Excellent
C: Slightly bad
D: Bad (2-2) Durability

Observation of a body cavity in a human body model was carried out by using each of the endoscopes which had been subjected to a bending operation property test. Thereafter, breakage of the optical fibers of the optical fiber bundles of the image guide and the light guide was examined, and the ratio of the broken optical fibers with respect to the entire optical fibers was evaluated according to the four criteria given below for each of the endoscopes.

A: The ratio of the broken optical fibers was less than 5%, and an observation image was extremely clear, B: The ratio of the broken optical fibers was equal to or more than 5% but less than 20%, and an observation image was clear so that diagnosis can be performed with almost no problem.

C: The ratio of the broken optical fibers was equal to or more than 20% but less than 50%, and an observation image was slightly dark.

D: The ratio of the broken optical fibers was more than 50%, and an observation image was dark so that there is a problem in performing diagnosis.

These results are shown in Table 1. The compositions of the lubricant used in each of the endoscopes were also shown in Table 1.

TABLE 1

| | | Lubricant | | | Evaluation | |
|---|---|---|---|---|---|---|
| | | Composition of | Mixing ratio [wt %] | | Covering | |
| | Part | Solid lubricant | Solid lubricant | silicone oil | Property | Durability |
| Example 1 | Bendable Part | BN | 5 | 95 | A | A |
| | Other Parts | — | 0 | 100 | | |
| Example 2 | Bendable Part | PTFE | 5 | 95 | A | A |
| | Other Parts | — | 0 | 100 | | |
| Example 3 | Bendable Part | $MoS_2$ | 2 | 98 | A | B |
| | Other Parts | — | 0 | 100 | | |
| Example 4 | Bendable Part | BN | 5 | 95 | A | A |
| | Other Parts | BN | 5 | 95 | | |
| Example 5 | Bendable Part | PTFE | 5 | 95 | A | A |
| | Other Parts | PTFE | 5 | 95 | | |
| Example 6 | Bendable Part | $MoS_2$ | 2 | 98 | A | B |
| | Other Parts | $MoS_2$ | 2 | 98 | | |
| Example 7 | Bendable Part | BN + PTFE | 5 | 95 | A | A |
| | Other Parts | BN | 5 | 95 | | |
| Com. Ex. 1 | Bendable Part | — | 0 | 100 | A | D |
| | Other Parts | — | 0 | 100 | | |
| Com. Ex. 2 | Bendable Part | BN | 100 | 0 | D | C |
| | Other Parts | BN | 100 | 0 | | |

TABLE 1-continued

| | | Lubricant | | | Evaluation | |
| | | Composition of | Mixing ratio [wt %] | | Covering | |
| | Part | Solid lubricant | Solid lubricant | silicone oil | Property | Durability |
|---|---|---|---|---|---|---|
| Com. Ex. 3 | Bendable Part | PTFE | 100 | 0 | D | D |
| | Other Parts | PTFE | 100 | 0 | | |
| Com. Ex. 4 | Bendable Part | MoS$_2$ | 100 | 0 | C | D |
| | Other Parts | MoS$_2$ | 100 | 0 | | |

As apparent from Table 1, in each of the endoscopes manufactured in Examples 1 to 7, the optical fibers were hard to be broken even after repeated use. Additionally, all the endoscopes had excellent durability.

Further, all the endoscopes of Examples 1 to 7 had excellent bending operation property, and they still had excellent bending operation property after repeated sterilization.

Furthermore, in each of the endoscopes manufactured in Examples 1 to 7, covering property of the optical fiber bundle with the protective sheath in manufacturing the endoscope was excellent.

On the other hand, the endoscopes of Comparative Examples 1 to 4 had poor durability. Further, in each of the endoscopes of Comparative Examples 2 to 4, covering property of the optical fiber bundle with the protective sheath in manufacturing the endoscope was also poor.

As has been described, according to the present invention, it is possible to obtain an endoscope which has small bending resistance and is hard to be damaged or broken even after repeated use.

Further, it is also possible to obtain an endoscope which has excellent chemical resistance and can be subjected to repeated high level sterilization.

These effects described above become more conspicuous by appropriately setting the conditions of the lubricant (e.g., the composition of the solid lubricant and the silicone oil, the mixing ratio thereof, and the like).

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2001-152545 (filed on May 22, 2001) which is expressly incorporated herein by reference in its entireties.

What is claimed is:

1. An endoscope, comprising:
 a plurality of lumens, each lumen having an interior space;
 at least one elongated member passing through the interior space of at least one of the lumens; and
 a lubricant distributed in the interior space of at least one of the lumens, the lubricant including a silicone oil and a solid lubricant containing polytetrafluoroethylene.

2. The endoscope according to claim 1, wherein the endoscope includes an insertion section having a bendable part, and the solid lubricant is distributed in at least the bendable part.

3. The endoscope according to claim 1, wherein the lubricant is distributed around the elongated member.

4. The endoscope according to claim 1, wherein the elongated member is an optical fiber bundle, and the silicone oil and the solid lubricant are distributed on at least a part of an outer surface of the optical fiber bundle.

5. The endoscope according to claim 1, wherein the elongated member is an optical fiber bundle, and the silicone oil and the solid lubricant are distributed on at least a part of an outer surface of respective optical fibers of the optical fiber bundle.

6. The endoscope according to claim 1, wherein the solid lubricant is a powder.

7. The endoscope according to claim 6, wherein an average grain size of the solid lubricant is in the range of 0.1 to 15 µm.

8. The endoscope according to claim 1, wherein the solid lubricant is dispersed in the silicone oil.

9. A The endoscope according to claim 1, wherein a kinematic viscosity of the silicone oil at 25° C. is 10 to 500 cst.

10. The endoscope according to claim 1, wherein the silicone oil contains modified silicone oils as its main ingredient.

* * * * *